United States Patent [19]

Ferguson

[11] Patent Number: 4,563,172

[45] Date of Patent: Jan. 7, 1986

[54] EMBRYO COLLECTOR AND COLLECTION METHOD

[75] Inventor: Bruce S. Ferguson, Buxton, Me.

[73] Assignee: ImmunoSystems, Incorporated, Biddeford, Me.

[21] Appl. No.: 567,745

[22] Filed: Jan. 3, 1984

[51] Int. Cl.[4] .......... A61M 31/00

[52] U.S. Cl. .......... 604/55; 128/1 R

[58] Field of Search .......... 210/474, 477, 299; 604/54, 55, 246, 252, 406; 128/1 R

[56] References Cited

U.S. PATENT DOCUMENTS

| | | | |
|---|---|---|---|
| 354,384 | 12/1886 | Bovey | 210/477 X |
| 1,605,887 | 11/1926 | Banks | 210/477 X |
| 2,675,000 | 4/1954 | Ford | 210/477 X |
| 2,742,849 | 4/1956 | Stiglitz | 210/477 X |
| 4,071,027 | 1/1978 | Meador | 604/55 |

FOREIGN PATENT DOCUMENTS

| | | | |
|---|---|---|---|
| 2070437 | 9/1981 | United Kingdom | 604/55 |

*Primary Examiner*—Ferris H. Lander
*Attorney, Agent, or Firm*—William Nitkin

[57] ABSTRACT

A device for collecting embryos carried in an irrigant fluid from the uterus of a mammal having a collection chamber into which the fluid is entered with a filter means disposed in the collection chamber through which the irrigant fluid is discharged leaving the embryos within the collection chamber for concentration and collection with a flow control member controlling the rate of discharge of the irrigant fluid from the collection chamber.

2 Claims, 1 Drawing Figure

EMBRYO COLLECTOR AND COLLECTION METHOD

BACKGROUND OF THE INVENTION

1. Field of the Invention

The device and method of this invention is in the area of the collection of embryos flushed from a mammalian uterus and more particularly relates to a device and method for concentrating and separating the embryos from the irrigant fluid.

2. History of the Prior Art

It is well known that mammalian embryos or ovum can be flushed from donor animals by inserting a tube through the cervix up into the uterine horn and causing an irrigant to pass through that tube to separate and carry the embryos and ovum, henceforth collectively referred to as embryos, from the uterine tissue to be drained through the tube out of the uterus and collected in plastic containers. The irrigant and suspended embryos are allowed to sit for a long period of time to allow the embryos to settle to the bottom of the container. The irrigant is either decanted off the top of the container or removed by the entry of a suction tube from above to syphon off the irrigant thereby leaving the concentrated embryos at the bottom of the plastic container.

SUMMARY OF THE INVENTION

It is an object of this invention to provide a new method and device for the concentrating of embryos carried in the irrigant fluid coming from the uterus of mammalian animals which eliminates the necessity of waiting long periods of time for the embryos to settle in the irrigant as in the prior art and which new device and method quickly and easily concentrate the embryos and further keep them substantially suspended in the irrigant fluid where they are protected.

The device of this invention comprises a collection chamber member into which enters the irrigant fluid with suspended embryos therein through the irrigant tube extending from the uterus. The irrigant tube can be affixed to and incorporated as a part of a cover which can snap on or be otherwise affixed over the collection chamber. The collection chamber is of a size small enough to hold at least 100–400 ml of irrigant fluid. At the base of the collection chamber is a filter through which the irrigant passes which filter, having a smaller mesh size than the size of the embryos, retains the embryos in the collection chamber. The irrigant, after passing through the mesh filter, passes through an irrigant discharge tube and its flow is controlled by a flow control member such as a thumb wheel or equivalent attached onto the irrigant discharge tube.

In practice utilizing, for example, a cow or other bovine, one superovulates and artificially inseminates the cow. The embryos are then flushed by one of many known methods from the horns of the uterus. As the irrigant flows out of the animal's vagina through the irrigant tube, it will pass into the device of this invention. In practice with a cow, 400–800 mls of fluid are flushed through the uterus. The device of this invention is attached onto the end of the irrigant tube and as the irrigant flushes out the bovine vagina through the irrigant tube, the irrigant flows through the irrigant tube into the collection chamber. The discharge of the device is regulated by flow control means which can be a thumbwheel, pinch clamp or similar flow-restricting device on the discharge tube of the device. The embryos flow into the collection chamber member and are collected therein as the irrigant fluid passes through a filter therein which will be described below. The embryos are too large to pass through this filter, and they are retained in the collection chamber, being concentrated in a smaller volume of fluid depending upon how much irrigant is allowed to flow out of the container by the user's action on the flow control member. Once the flushing of the uterus has ceased and the desired amount of irrigant surrounds the embryos now concentrated in the collection chamber, the cover of the device is removed and the contents poured into a petri dish for a visual search for suitable embryos.

The device and method of this invention can also be used to collect cells, salts, stones and other biologically significant material which is discharged through a catheter attached to a tube inlet on the cover of the collection chamber member. The filter mesh size would be changed so that the size of its openings would be smaller than the size of the biological material being collected.

One can use the flow control member so that the exit flow of the irrigant through the filter into the irrigation discharge tube is slow enough to keep a volume of fluid in the collection chamber so that with minimal manual shaking of the collection chamber, the embryos will be kept in suspension to prevent their falling against the filter or one another and to prevent pressure from being placed upon the embryos by other tissues or other embryos coming to rest on top of them due to the force of fast-moving irrigant discharge through the filter of the device of this invention. The flow control member can allow the irrigant to leave the collection chamber through the filter by the user judging from looking through either a transparent or translucent collection chamber, how much fluid is within the collection chamber at all times and allowing sufficient amount of fluid to remain therein at the end of the collection process so as to be able to pour the embryos and other cellular debris easily into the petri dish for visual examination. This collection method saves many hours over the prior method of embryo settling and in practice has been found to be most successful.

It should be noted that the size of the collection chamber can vary to accommodate irrigant flushing for different animals which may require different amounts of irrigant fluid for successful flushing of the embryos out of the uterus.

A typical filter such as a 75 micron filter can be snapped into the base of the collection chamber and held in place by a filter retention lip, but any other means of attaching the filter to the base of the collection chamber will suffice. Further the cap should fit on the collection chamber either by snapping or screwing in a fluid-tight relation so that no irrigant will spill out through the top and cause valuable embryos to become lost.

DESCRIPTION OF THE PREFERRED EMBODIMENT(S)

Figure 1:
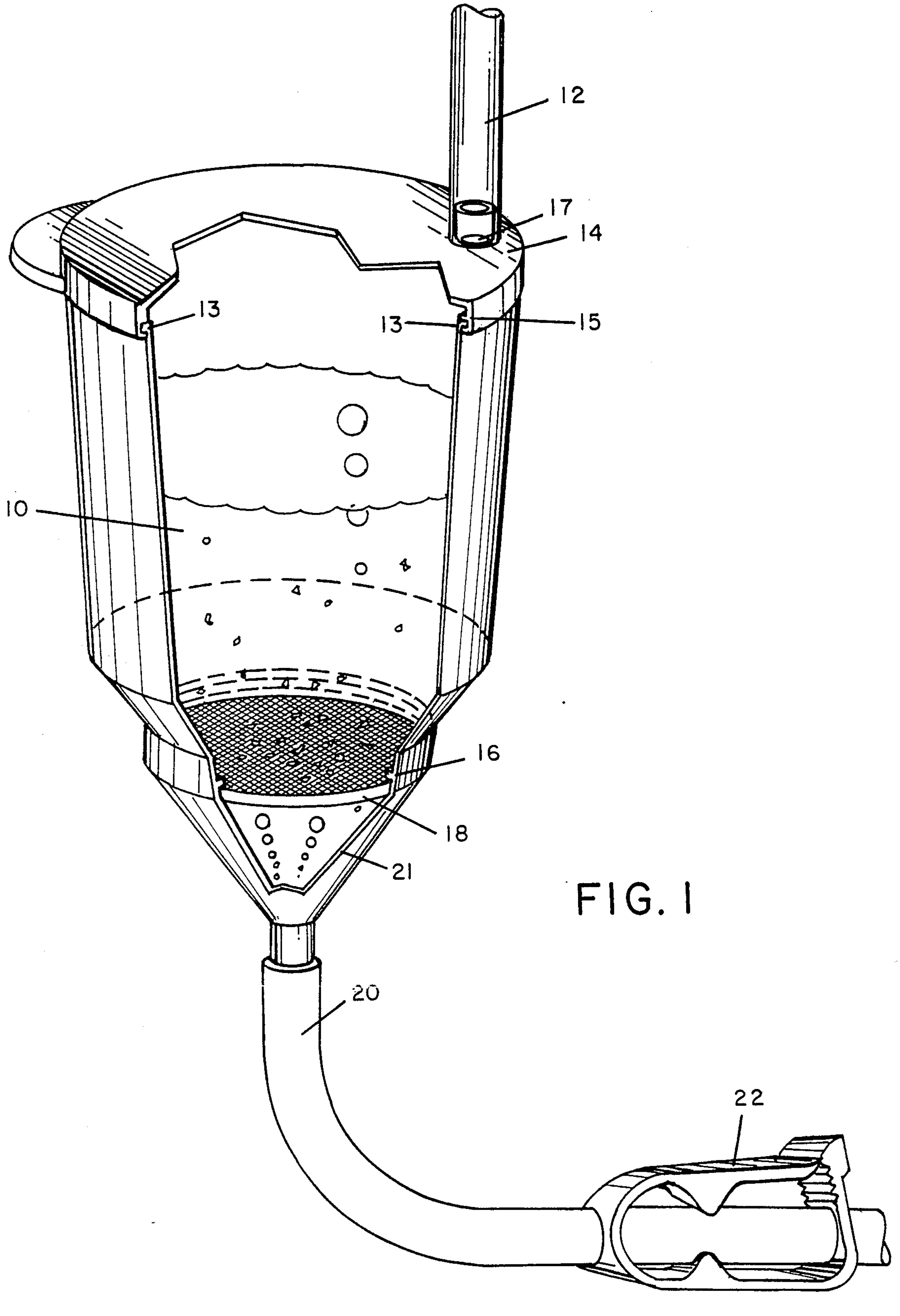
FIG. 1 illustrates a perspective cutaway view of the device of this invention.

FIG. 1 illustrates a perspective cutaway view of the device of this invention showing collection chamber 10 having cover 14 affixed thereof. Cover 14 can be affixed thereon by snapping, such as shown herein with small lips 13 and 15 being formed on the collection chamber and on the inner side of the cover. Other methods of attaching the cover could be utilized such as friction fit or screw-on fit. Cover 14 has attached on a portion thereof irrigant tube 12 which allows irrigant fluid to enter therethrough and pass through aperture 17 in the cover itself. This design allows the irrigant or other fluid passing through any tube or catheter to be attached to cover 14 and to pass through the top of cover 14 to enter collection chamber 10. At the bottom of collection chamber 10 is filter retention member 16 which can take the form of a lip which extends over filter 18 but any equivalent method of providing a filter at the base of the collection chamber can be utilized, for example, by forming a separate member that screws on with a filter therein. The filter can be of many types as long as the size of the openings in the filter is smaller than the size of the embryos or other materials being collected. An example would be a filter to collect some tissue of above 75 microns in size but will pass smaller tissue and debris into the irrigant discharge tube 20 below. It should be noted that the filter size relates to what biological material is to be collected, and the type of filter can be changed to collect those different materials within the collection chamber. On irrigant discharge tube 20 is flow control member 22 which can be a thumb wheel, pinch clamp or any similar well-known flow-restricting device in a tube.

In practice one would use the prior art methods of entering irrigant into the uterus of the mammal from which the embryos are to be removed and allow the discharge tube to be irrigant tube 12. The discharged irrigant carrying the embryos or other material to be collected would pass through cover 14 into collection chamber 10 and pass down to filter 16 where the irrigant and materials smaller than the filter size would pass through the filter into irrigant discharge tube 20. Chamber 21 having a funnel shape can be located below the filter to carry the irrigant to discharge tube 20. Flow control member 22 would control the rate of the irrigant and smaller debris passing through filter 18 once the fluid has backed up to the filter in chamber 21. It is desired in this method of collecting that the flow control member be operated slowly to allow a volume of fluid to build up in collection chamber 10 and that the contents of the collection chamber be either shaken or otherwise moved by the turbulence of the irrigant entering into the chamber so that the fluid will be in movement causing the embryos not to rest on the top of the filter. Once the irrigant fluid has been discharged from the uterus, the flow control member will allow the user to remove the volume of irrigant from the collection chamber as desired, leaving a volume of irrigant in the collection chamber so that the embryos can be poured into a petri dish for examination. Fluid held above flow control member 22 in chamber 21 and within the discharge tube should not significantly flow back into the collection chamber when it is being emptied as there is no air pressure thereabove since the flow control member would be closed. What minor amount of fluid that may leak back through the filter 18 when the collection chamber is being poured out.will not significantly affect the desired results.

Although the present invention has been described with reference to particular embodiments, it will be apparent to those skilled in the art that variations and modifications can be substituted therefor without departing from the principles and spirit of the invention.

I claim:

1. A device for concentrating and collecting embryos from an irrigant fluid coming from the uterus of a mammal, comprising:

a substantially transparent collection chamber having an open top and an open bottom;

an irrigant tube extending from the uterus of a mammal to enter embryo-carrying fluid coming from said uterus into said collection chamber;

a filter having a filtering mesh of a size smaller than the size of the embryos to be collected positioned at the open bottom of said collection chamber;

filter retention means to hold said filter at the bottom of said collection chamber;

a funnel-shaped receipt chamber positioned beneath said filter having an aperture defined in the bottom thereof;

a discharge tube affixed to said receipt chamber around said aperture adapted to receive fluid passing through said filter, said receipt chamber and said receipt chamber aperture;

a flow control member adapted to control the rate of discharge of fluid through the discharge tube from said collection chamber to maintain by its operation a sufficient level of fluid in said collection chamber combined with gentle agitation of the collection chamber to prevent the embryos from falling to the filter; and a cover member having an aperture defined therein through which said irrigant tube enters embryo-carrying fluid into said collection chamber, said cover removably affixed in fluid-tight relationship over the open top of said collection chamber.

2. A method for the collection and concentration of embryos out of an irrigant fluid from a mammalian uterus, comprising:

passing said embryo-carrying fluid out of said uterus;

collecting said fluid in a substantially transparent collection chamber having a removable fluid-tight cover by passing said fluid through an aperture defined in said cover;

providing a filter at the base of said collection chamber;

passing said fluid through said filter;

retaining said embryos in said collection chamber by action of said filter;

collecting said fluid after passing it through said filter in a receipt chamber;

discharging the fluid from said receipt chamber through a discharge tube;

controlling the rate of flow of fluid in said discharge tube by a flow control member;

observing the fluid level in said collection chamber;

maintaining a sufficient level of fluid in said collection chamber to keep said embryos in suspension by controlling the flow of said fluid by allowing said fluid to back up through said receipt chamber and filter into said collection chamber;

gently agitating said fluid in said collection chamber;

maintaining said embryos in suspension in said fluid in said collection chamber while discharging said fluid;

preventing said embryos from falling against said filter by said maintaining said embryos in suspension and said gentle agitation;

maintaining sufficient fluid in said collection chamber to keep said embryos in suspension at the completion of passing said embryo-carrying fluid from said uterus;

removing said cover from said collection chamber;

pouring the concentrated collected embryos, after the completion of the passing of said fluid through said collection chamber except for said sufficient fluid necessary to maintain said embryos in suspension, into a container for examination thereof.

* * * * *